United States Patent [19]

Fick

[11] Patent Number: 5,945,100
[45] Date of Patent: Aug. 31, 1999

[54] TUMOR DELIVERY VEHICLES

[75] Inventor: James R. Fick, Martinez, Ga.

[73] Assignee: FBP Corporation, San Francisco, Calif.

[21] Appl. No.: 08/690,535

[22] Filed: Jul. 31, 1996

[51] Int. Cl.[6] .................................................. A01N 63/00
[52] U.S. Cl. .................................... 424/93.21; 424/78.01; 424/428; 424/488; 424/497; 435/455; 435/320.1; 435/325
[58] Field of Search .................................. 514/44; 435/6, 435/7.23, 455, 320.1, 325; 424/488, 497, 78.01, 428, 93.21; 604/51; 935/57, 9

[56] References Cited

U.S. PATENT DOCUMENTS

| | | | |
|---|---|---|---|
| 4,352,883 | 10/1982 | Lim | 435/178 |
| 4,868,116 | 9/1989 | Morgan et al. | 435/240.2 |
| 4,980,286 | 12/1990 | Morgan et al. | 435/172.3 |
| 5,441,732 | 8/1995 | Hoeg et al. | 424/78.04 |
| 5,552,309 | 9/1996 | March | 435/172.3 |
| 5,599,534 | 2/1997 | Himmelstein et al. | 424/78.04 |
| 5,652,225 | 7/1997 | Isner | 514/44 |
| 5,656,481 | 8/1997 | Baetge et al. | 435/325 |
| 5,770,580 | 6/1998 | Ledley et al. | 514/44 |

FOREIGN PATENT DOCUMENTS

| | | |
|---|---|---|
| WO 89/07136 | 8/1989 | WIPO . |
| WO 90/02806 | 3/1990 | WIPO . |
| WO 93/17669 | 9/1993 | WIPO . |
| WO 94/25080 | 10/1994 | WIPO . |
| WO 96/20732 A2 | 7/1996 | WIPO . |
| WO 96/21470 A2 | 7/1996 | WIPO . |
| WO 97/28179 A1 | 8/1997 | WIPO . |

OTHER PUBLICATIONS

Ledley (1995) Hum. Gene Ther. 6:1129–44
Ronald Crystal (1995) Science, vol. 270:404–409
Coglan (Nov. 1995) New Scientist, pp. 14–15.
Park (1993) Adv. Drug Del. Rev. 11:59–84.
Kuo et al. (1996) Crit. Rev. Eukar. Gene Expression, 6(1):68.
Jain (1994) Scientific America, 271(1):58–63.
Monsigny et al. (1995) Adv. Drug Delivery Rev. 14:1–24.
Petrak (1993) Particulate Carrier, Ronald Allan (1993), pp. 275–293.
Gunzburg et al., vol. 1, No. 9, pp. 410–417, 1995.
Mastrangelo et al. (Seminars in Oncology, 1996, vol. 23, 1:4–21).
Colombo, et al., "The 'Bystander Effect': Association of U–87 Cell Death with Ganciclovir–Mediated Apoptosis of Nearby Cells and Lack of Effect in Athymic Mice," *Human Gene Therapy* 6:763–772 (1992).
Fick, et al., "The extent of heterocellular communication mediated by gap junctions is predictive of bystander tumor cytotoxicity in vitro," *Proc. Natl. Acad. Sci. USA* 92:11071–11075 (1995).

Alkan–Onyuksel, et al., "A Mixed Micellar Formulation Suitable for the Parental Administration of Taxol" Pharm. REs. 11(2), 206–212 (1994).
Bagshawe, K.D., "Towards generating cytotoxic agents at cancer sites" *Br. J. Cancer*, 60:275–281, (1989).
Bagshawe, et al., "A cytotoxic agent can be generated selectively at cancer sites" *Br. J. Cancer*, 58:700–703 (1988).
Balzarini, et al., "Differential Mechanism of Cytostatic Effect of (E)–5–(2–Bromovinyl)–2'–deoxyuridine, 9–(1, 3–Dihydroxy–2–propoxymethyl)guanine, and Other Antiherpetic Drugs on Tumor Cells Transfected by the Thymidine Kinase Gene of Herpes Simplex Virus Type 1 or Type 2" *J. Biol. Chem.*, 268:6332–6337 (1993).
Battelli, et al., "T lymphocyte killing by a xanthine–oxidase–containing immunotoxin" *Cancer Immunol. Immunother.*, 35:421–425 (1992).
Berkner et al., 1987 "Abundant Expression of Polyomavirus Middle T Antigen and Dihydrofolate Reductase in an Adenovirus Recombinant" *J. Virology* 61:1213–1220 (1987).
Bout, "Lung Gene Therapy: In Vivo Adenovirus–Mediated Gene Transfer to Rhesus Monkey Airway Epithelium" *Human Gene Therapy* 5:3–10 (1994).
Brem et al., "Intraoperative Chemotherapy using biodegradable polymers: Safety and Effectiveness for Recurrent Glioma Evaluated by a Prospective, Multi–Institutional Placebo–Controlled Clinical Trial" *Proc. Amer. Soc. Clin. Oncology* (May 17, 1994).
Brem, et al., Interstitial chemotherapy with drug polymer implants for the treatment of recurrent gliomas *J. Neurosurg.* 74:441–446 (1991).
*Brem, et al., "Polymers as Controlled Drug Delivery Devices for the Treatment of Malignant Brain Tumors" *Eur. J. Pharm. Biopharm.* 39(1):2–7 (1993).
Brown and Burlingham, "Penetration of Host Cell Membranes by Adenovirus 2" *J. Virology* 12:386–396 (1973).
*Brown and Greene, DNA and Cell Biology 10(6):399–409 (1991).

(List continued on next page.)

*Primary Examiner*—Bruce R. Campell
*Assistant Examiner*—Dave Trong Nguyen
*Attorney, Agent, or Firm*—Arnall Golden & Gregory, LLP

[57] ABSTRACT

The major problem with current direct delivery techniques of therapeutic reagents into solid tumors, especially of cells or large volumes of recombinant DNA reagents or drugs, has been resistance of the tissues to the influx of the fluid and/or cells, resulting in low quantities of the fluid and/or cells penetrating into and remaining in the tumor tissue to be treated. Increased penetration and/or reduced backflow and diversion through the point of entry, so that more material is introduced into and remains in the tumor, is obtained through the use of a viscous vehicle, most preferably having a similar density to tissue, for the material to be delivered. Preferred materials include solutions or suspensions of a polymeric material which gel or solidify at the time of or shortly after injection or implantation. In the preferred embodiment, the solution is injected via a catheter into regions of the tumor to be treated.

18 Claims, No Drawings

OTHER PUBLICATIONS

Bruce and Meeker, "Comparison of the Sensitivity of Hematopoietic Colony–Forming Cells in Different Proliferative States to 5–Fluorouracil" *J. Natl. Cancer Inst.*, 38:401–405 (1967).

Caillaud et al., "Adenoviral Vector as a Gene Delivery System into Cultured Rat Neuronal and Glial Cells" *Eur. J. Neuroscience* 5:1287–1291 (1993).

Chardonnet and Dales, "Early Events in the Interaction of Adenoviruses with HeLa cells: I. Penetration of Type 5 and Intracellular Release of the DNA Genome" *Virology* 40:462–477 (1970).

Concise Encyclopedia of Polymer Science and Polymeric Amines and Ammonium Slats, E. Goethals, editor (Pergamon Press, Elmsford, NY 1980).

Culver, et al., "In Vivo Gene Transfer with Retroviral Vector–Produced Cells for Treatment of Experimental Brain Tumors" *Science* 256:1550–1552 (1992).

Davidson et al., "Overproduction of Polyomavirus Middle T Antigen in Mammalian Cells through the Use of an Adenovirus Vector" *J. Virology* 61:1226–1239 (1987).

Gomez–Foix, "Adenovirus–mediated Transfer of the Muscle Glycogen Phosphorylase Gene into Hepatocytes Confers Altered Regulation of Glycogen Metabolism" *J. Biol. Chem.* 267:25129–25134 (1992).

Gottlieb, J.A., and J.K. Luce, "Treatment of Malignant Melanoma with Camptothecin" *Cancer Chemother. Rep.* 56(1):103–105 (1972).

Guzman, "Efficient Gene Transfer Into Myocardium by Direct Injection of Adenovirus Vectors" *Circulation Research* 73:1201–1207 (1993)

Haj–Ahmad et al,. "Development of a Helper–Independent Human Adenovirus Vector and Its Use in the Transfer of the Herpes Simplex Virus Thymidine Kinase Gene" *J. Virology* 57:267–274 (1986).

Harrison's Principles of Internal Medicine 431–446, E. Braunwald, et al., ed., McGraw–Hill Book Co. (1987).

Hughes et al., "Monoclonal Antibody Targeting of Liposomes to Mouse Lung in Vivo" *Cancer Research*, 49:6214–6220, (1989).

Kirshenbaum, *J. Clin. Invest.* 92:381–387 (1993).

La Salle, "An Adenovirus Vector for Gene Transfer into Neurons and Glia in the Brain" *Science* 259:988–900 (1993).

Langer, R., and D. Wise, eds, Medical Applications of Controlled Release, vol. I and II, Boca Raton, CRC Press (1986).

Litzinger and Huang, "Biodistribution and immunotargetability of ganglioside–stabilized dioleoylphosphatidylethanolamine liposomes" *Biochmimica et Biophysica Acta*, 1104:179–187, 1992).

Massie et al., "Construction of a Helper–Free Recombinant Adenovirus That Expresses Poluomavirus Large T Antigen" *Mol. Cell. Biol.* 6:2872–2883 (1986).

* Matsuda et al., *AsAID Trans.*, 38:154–157 (1992).

Moertel, C.G., et al., "Phase II Study of Camptothecin (NSC–100880) in the Treatment of Advanced Gastrointestinal Cancer" *Cancer Chemother. Rep.* 56(1):95–101 (1972).

Morsy, "Efficient Adenoviral–mediated Ornithine Transcarbamylase Expression in Deficient Mouse and Human Hepatocytes" *J. Clin. Invest.* 92:1580–1586 (1993).

Mouller, "Correction of lysosomal storage in the liver and spleen of MPS VII mice by implantation of genetically modified skin fibroblasts" *Nature Genetics* 4:154–159 (1993).

Muggia, F.M., et al., "Phase I Clinical Trial of Weekly and Daily Treatment with Camptothecin (NSC–100880): Correlation With Preclinical Studies" *Cancer Chemother. Rep.* 56(4):515–521 (1972).

Mullen, C.A., "Transfer of the bacterial gene for cytosine deaminase to mammalian cells confers lethal sensitivity to 5–fluorocytosine: A negative selection system" *Proc. Natl. Acad. Sci.* 89:33–37 (1992).

Mulligan, "The Basic Science of Gene Therapy" *Science* 260:926–932 (1993).

Petrie, C.R., et al., "A Novel Biotinylated Adenylate Analogue Derived from Pyarzolo[3,4–d]pyrimidine for Labeling DNA Probes" *Bioconjugate Chem.* 2:441–446 (1991).

Pietersaz and McKnezie, "Antibody Conjugates for the Treatment of Cancer" *Immunolog. Reviews,* 129:57–80, (1992).

Ragot, T., et al,. "Replication–defective recombinant adenovirus expressing the Epstein–Barr virus (EBV) envelope glycoprotein gp340/220 induces protective immunity against EBV–induced lymphomas in the cottontop tamarin" *J. Gen. Virology* 74:501–507 (1993).

Ram et al., "In Situ Retroviral–mediated Gene Transfer for the Treatment of Brain Tumors in Rats" *Cancel Res.*, 53:83–88 (1993).

Rich, "Development and Analysis of Recombinant Adenoviruses for Gene Therapy of Cystic Fibrosis" *Human Gene Therapy* 4:461–476 (1993).

Roessler, "Adenoviral–mediated Gene Transfer to Rabbit Synovium In Vitro" *J. Clin. Invest.* 92:1085–1092 (1993).

Roffler, et al., "Anti–neoplastic glucuronide prodrug treatment of human tumor cells targeted with a monoclonal antibody–enzyme conjugate" *Biochemical Pharm.* 42:2062–2065, 1991.

Sarosy and Reed, "Taxol Dose Intensification and its Clinical Implications" *J. Nat. Med. Assoc.* 85(6):427–431 (1993).

* Senter, et al., "A Novel Biotinylated Adenylate Analogue Derived from Pyrazolo[3,4–d]pyrimidine for Labeling DNA Probes," *Bioconjugate Chem.*, 2(1):447–451, (1991).

Senter, et al., "Generation of Cytotoxic Agents by Targeted Enzymes," *Bioconjugate Chem.*, 4(1):3–9, (1993).

Seth, et al., "Evidence that the Penton Base of Adenovirus Is Involved in Potentiation of Toxicity of Pseudomonas Exotoxin Conjugated to Epidermal Growth Factor" *Mol. Cell. Biol.* 5:1528–1533 (1984).

* Seth, et al., *J. Virol.* 51:650–655 (1984).

Sporn and Roberts, eds., "Peptide Growth Factors and Their Receptors 1" eds. (Springer–Verlag, New York, 1990).

Steinleitner et al., "An evaluation of Flowgel* as an intraperitoneal barrier for prevention of postsurgical adhesion reformation" *Fertility and Sterility* 57:305–308 (1992).

Steinleitner et al., "Poloxamer 407 as an Intraperitoneal Barrier Material for the Prevention of Postsurgical Adhesion Formation and Reformation in Rodent Models for Reproductive Surgery" *Obstetrics & Gynecology*, 77:48–52 (1991).

Svensson, "Role of Vesicles During Adenovirus 2 Internalization into HeLa Cells" *J. Virology* 55:442–449 (1985).

T. Tomita, "Interstitial chemotherapy for brain tumors: review" *J. Neuro–Oncology* 10:57–74 (1991).

Varga et al., "Infectious Entry Pathway of Adenovirus Type 2" *J. Virology* 65:6061–6070 (1991).

Venditti, J.M., and B.J. Abbott, "Studies on Oncolytic Agents from Natural Sources. Correlations of Activity Against Animal Tumors and Clinical Effectiveness" *Lloydia* 30:332–348 (1967).

Verma, I.M., "Retroviral vectors for gene transfer," in *Microbiology–1985*, American Society for Microbiology, 229–232, (1985).

Wickham et al., "Integrins $\alpha_v\beta_3$ and $\alpha_v\beta_5$ Promote Adenovirus Internalization but Not Virus Attachment" *Cell* 73:309–319 (1993).

Zabner, "Safety and efficacy of repetitive adenovirus–mediated transfer of CFTR cDNA to airway epithelia of primates and cotton rats" *Nature Genetics* 6:75–83 (1994).

Zabner, "Adenovirus–Mediated Gene Transfer Transiently Corrects the Chloride Transport Defect in Nasal Epithelia of Patients with Cystic Fibrosis" *Cell* 75:207–216 (1993).

Zhang, "Generation and identification of recombinant adenovirus by liposome–mediated transfection and PCR analysis" *BioTechniques* 15:868–872 (1993).

TUMOR DELIVERY VEHICLES

BACKGROUND OF THE INVENTION

The present invention is generally in the area of delivery vehicles, for therapeutic agents for the treatment of tumors, especially brain tumors.

One-third of all individuals in the United States alone will develop cancer. Although the five-year survival rate has risen dramatically to nearly fifty percent as a result of progress in early diagnosis and the therapy, cancer still remains second only to cardiac disease as a cause of death in the United States. Twenty percent of Americans die from cancer, half due to lung, breast, and colon-rectal cancer.

Designing effective treatments for patients with cancer has represented a major challenge. The current regimen of surgical resection, external beam radiation therapy, and/or systemic chemotherapy has been partially successful in some kinds of malignancies, but has not produced satisfactory results in others. In some malignancies, such as brain malignancies, this regimen produces a median survival of less than one year. For example, 90% of resected malignant gliomas recur within two centimeters of the original tumor site within one year.

Though effective in some kinds of cancers, the use of systemic chemotherapy has had minor success in the treatment of cancer of the colon-rectum, esophagus, liver, pancreas, and kidney and melanoma. A major problem with systemic chemotherapy for the treatment of these types of cancer is that the systemic doses required to achieve control of tumor growth frequently result in unacceptable systemic toxicity. Efforts to improve delivery of chemotherapeutic agents to the tumor site have resulted in advances in organ-directed chemotherapy, as by continuous systemic infusion, for example. However, continuous infusions of anticancer drugs generally have not shown a clear benefit over pulse or short-term infusions. Implantable elastomer access ports with self-sealing silicone diaphragms have also been tried for continuous infusion, but extravasation remains a problem. Portable infusion pumps are now available as delivery devices and are being evaluated for efficacy. (See *Harrison's Principles of Internal Medicine* 431–446, E. Braunwald et al., ed., McGraw-Hill Book Co. (1987) for a general review).

In the brain, the design and development of effective anti-tumor agents for treatment of patients with malignant neoplasms of the central nervous system have been influenced by two major factors: 1) the blood-brain barrier provides an anatomic obstruction in the normal brain, potentially limiting access of drugs to some regions of the tumors; and 2) the drugs given at high systemic levels are generally cytotoxic. Efforts to improve drug delivery to the tumor bed in the brain have included transient osmotic disruption of the blood brain barrier, cerebrospinal fluid perfusion, local delivery from implanted polymeric controlled release devices and direct infusion into a brain tumor using catheters. Each technique has had significant limitations. Disruption of the blood brain barrier increased the uptake of hydrophilic substances into normal brain, but did not significantly increase substance transfer into the tumor. Only small fractions of agents administered into the cerebrospinal fluid actually penetrated into the brain parenchyma. Controlled release biocompatible polymers for local drug delivery have been utilized for contraception, insulin therapy, glaucoma treatment, asthma therapy, prevention of dental caries, and certain types of cancer chemotherapy. (Langer, R., and D. Wise, eds, *Medical Applications of Controlled Release*, Vol. I and II, Boca Raton, CRC Press (1986)) Brain tumors have been particularly refractory to chemotherapy. One of the chief reasons is the restriction imposed by the blood-brain barrier. Agents that appear active against certain brain tumors, such as gliomas, in vitro may fail clinical trials because insufficient drug penetrates the tumor. Although the blood-brain barrier is disrupted at the core of a tumor, it is largely intact at the periphery where cells actively engaged in invasion are located. Experimental intratumoral regimens include infusing or implanting therapeutic agents within the tumor bed following surgical resection, as described by Tomita, T, *J. Neuro-Oncol.* 10: 57–74 (1991). Drugs that have been used to treat tumors by infusion have been inadequate, did not diffuse an adequate distance from the site of infusion, or could not be maintained at sufficient concentration to allow a sustained diffusion gradient. The use of catheters has been complicated by high rates of infection, obstruction, and malfunction due to clogging. See T. Tomita, "Interstitial chemotherapy for brain tumors: review" *J. Neuro-Oncology* 10: 57–74 (1991).

Delivery of a low molecular weight, lipid soluble chemotherapeutic, 1,3-bis(2-chloroethyl)-1-nitrosourea (BCNU), in a polymer matrix implanted directly adjacent to brain tumors has some efficacy, as reported by Brem, et al., *J. Neurosurg.* 74: 441–446 (1991); Brem, et al., *Eur. J. Pharm. Biopharm.* 39(1): 2–7 (1993); and Brem, et al., "Intraoperative Chemotherapy using biodegradable polymers: Safety and Effectiveness for Recurrent Glioma Evaluated by a Prospective, Multi-Institutional Placebo-Controlled Clinical Trial" *Proc. Amer. Soc. Clin. Oncology* May 17, 1994. Polymer-mediated delivery of BCNU was superior to systemic delivery in extending survival of animals with intracranial 9L gliosarcoma and has shown some efficacious results in clinical trials. However, BCNU is a low molecular weight drug, crosses the blood-barrier and had previously been demonstrated to have some efficacy when administered systemically.

For example, one promising chemotherapeutic, camptothecin, a naturally occurring alkaloid isolate from *Camptotheca acuminata*, a tree indigenous to China, which exerts its pharmacological effects by irreversibly inhibiting topoisomerase I, an enzyme intimately involved in DNA replication, has been shown to have strong cytotoxic anti-tumor activity against a variety of experimental tumors in vitro, such as the L1210 and rat Walker 256 carcinosarcoma (Venditti, J. M., and B. J. Abbott, *Lloydia* 30: 332–348 (1967); Moertel, C. G., et al., *Cancer Chemother. Rep.* 56(1): 95–101 (1972)). Phase I and II clinical trials of camptothecin in human patients with melanoma and advanced gastrointestinal carcinoma, however, have shown unexpectedly severe systemic toxicity with poor tumoral responses, and clinical investigation therefore halted. (Gottlieb, J. A., and J. K. Luce, *Cancer Chemother. Rep.* 56(1): 103–105 (1972); Moertel, C. G., et al., *Cancer Chemother. Rep.* 56(1): 95–101 (1972); Muggia, F. M., et al., *Cancer Chemother. Rep.* 56(4): 515–521 (1972)). Many other chemotherapeutics which are efficacious when administered systemically must be delivered at very high dosages in order to avoid toxicity due to poor bioavailability. For example, paclitaxel (taxol) has been used systemically with efficacy in treating several human tumors, including ovarian, breast, and non-small cell lung cancer. However, maintenance of sufficient systemic levels of the drug for treatment of tumors has been associated with severe, in some cases "life-threatening" toxicity, as reported by Sarosy and Reed, *J. Nat. Med. Assoc.* 85(6): 427–431 (1993). Paclitaxel is a high molecular weight (854), highly lipophilic deterpenoid isolated from the western yew, *Taxus brevifolia*, which is insoluble in water. It is normally administered intravenously by dilution into saline of the drug dissolved or suspended in polyoxyethylated castor oil. This carrier has been reported to induce an anaphylactic reaction in a number of patients (Sarosy and Reed (1993)) so alternative carriers have been proposed, such as a mixed micellar formulation for parenteral administration, described by Alkan-Onyuksel, et al., *Pharm. Res.* 11(2), 206–212 (1994).

Gene transfer is rapidly becoming a useful adjunct in the development of new therapies for human malignancy. Tumor cell expression of histocompatibility antigens, cytokines, or growth factors (e.g., IL-2, IL-4, GMCSF) appears to enhance immune-mediated clearance of malignant cells in animal models, and expression of chemoprotectant gene products, such as p-glycoprotein in autologous bone marrow cells, is under study as a means of minimizing marrow toxicity following administration of otherwise lethal doses of chemotherapeutic agents.

Theoretically, the most direct mechanism for tumor cell killing using gene transfer is the selective expression of cytotoxic gene products within tumor cells. Classical enzymatic toxins such as pseudomonas exotoxin A, diphtheria toxin and ricin are unlikely to be useful in this context, since these enzymes kill only cells in which they are expressed, and no current gene transfer vector is capable of gene delivery to a sufficiently high percentage of tumor cells to make use of the above recombinant enzymes.

Another strategy that has been developed to selectively kill tumor cells involves the delivery to replicating tumor cells and expression of genes encoding toxic prodrugs such as the Herpes simplex virus thymidine kinase (HSV-tk) gene followed by treatment with ganciclovir. Ganciclovir is readily phosphorylated by the HSV-tk, and its phosphorylated metabolites are toxic to the cell. Very little phosphorylation of ganciclovir occurs in normal human cells. Although only those cells expressing the HSV-tk should be sensitive to ganciclovir (since its phosphorylated metabolites do not readily cross cell membranes), in vitro and in vivo experiments have shown that a greater number of tumor cells are killed by ganciclovir treatment than would be expected based on the percentage of cells containing the HSV-tk gene. This unexpected result has been termed the "bystander effect" or "metabolic cooperation". It is thought that the phosphorylated metabolites of ganciclovir may be passed from one cell to another through gap junctions.

Although the bystander effect has been observed in initial experiments using HSV-tk, the limitations present in all current gene delivery vehicles mean that a much greater bystander effect than previously noted will be important to successfully treat human tumors using this approach. One of the difficulties with the current bystander toxicity models is that bystander toxicity with metabolites that do not readily cross the cell membrane will not be sufficient to overcome a low efficiency of gene transfer (e.g., transfection, transduction, etc.). In the known toxin gene therapy systems, the efficiency of transduction and/or transfection in vivo is generally low. An existing protocol for treating brian tumors in humans uses retroviral delivery of HSV-tk, followed by ganciclovir administration. In rat models, using HSV-tk in this context, tumor regressions have been observed (Culver, et al., *Science,* 256: 1550–1552 (1992). The HSV-tk approach has not proven sufficient in humans thus far, although some tumor regressions have been observed.

Similarly, the usefulness of *E. coli* cytosine deaminase (which converts 5-fluorocytosine to 5-fluorouracil and could theoretically provide substantial bystander toxicity) in this regard remains to be established. Initial studies have shown that cytosine deaminase expression followed by treatment with 5-fluorocytosine in clonogenic assays leads to minimal bystander killing (C. A., Mullen, C. A., M. Kilstrup, R. M. Blaese, *Proc. Natl. Acad. Sci. USA,* 89: 33–37 (1992).

Prodrug activation by an otherwise non-toxic enzyme (e.g., HSV-tk, cytosine deaminase) has advantages over the expression of directly toxic genes, such as ricin, diphtheria toxin, or pseudomonas exotoxin. These advantages include the capability to titrate cell killing, optimize therapeutic index by adjusting either levels of prodrug or of recombinant enzyme expression, and interrupt toxicity by omitting administration of the prodrug. However, like other recombinant toxic genes, gene transfer of HSV-tk followed by treatment with ganciclovir is neither optimized to kill bystander cells nor is it certain bystander toxicity will occur in vivo as has been characterized in vitro. An additional problem with the use of the HSV-tk or cytosine deaminase to create toxic metabolites in tumor cells is the fact that the agents activated by HSV-tk (ganciclovir, etc.) and cytosine deaminase (5-fluorocytosine) will kill only cells that are synthesizing DNA (Balzarini, et al., *J. Biol. Chem.,* 268: 6332–6337 (1993), and Bruce and Meeker, *J. Natl. Cancer Inst.,* 38: 401–405 (1967). Even if a considerable number of nontransfected cells are killed, one would not expect to kill the nondividing tumor cells with these agents.

It is therefore an object of the present invention to provide vehicles that increase the efficiency of delivery of therapeutic reagents, including viral vectors, cells, nucleic acids, antibodies and other proteins, lipids, and carbohydrates, to tumors, especially brain tumors.

It is a further object of the present invention to provide vehicles that are useful for direct delivery into tumors of drugs in solid or liquid form, as well as genetic material, including genetic material contained within cells.

SUMMARY OF THE INVENTION

The major problem with current direct delivery techniques of therapeutic reagents into solid tumors, especially of cells or large volumes of recombinant DNA reagents or drugs, has been resistance of the tissues to the influx of the fluid and/or cells, resulting in low quantities of the fluid and/or cells penetrating into and remaining in the tumor tissue to be treated. Increased penetration and/or reduced backflow and diversion through the point of entry, so that more material is introduced into and remains in the tumor, is obtained through the use of a viscous vehicle, most preferably having a similar density to tissue, for the material to be delivered. Preferred materials include solutions or suspensions of a polymeric material which gel or solidify at the time of or shortly after injection or implantation. In the preferred embodiment, the solution is injected via a catheter into regions of the tumor to be treated.

DETAILED DESCRIPTION OF THE INVENTION

The general criteria for vehicles for delivery to solid tumors are that the materials must not inactivate the chemotherapeutic agent and must impart to the delivered material a density or viscosity similar to that of tissue.

Materials to be Delivered

As used herein, chemotherapeinic agents include synthetic organic or inorganic drugs, biologically active materials which replace or supplement a normal function such as hormones, angiogenic or anti-angiogenic factors, immunomodulators, and cytotoxic agents such as plantinum based chemotherapeutics, for example, cisplantinum, BCNU and other nitrosourea compounds, cytokines, and others known to those skilled in the art, and genetically engineered materials. Genetically engineered materials include RNA or DNA encoding a toxin, ribozymes, external guide sequences for RNAase P, antisense, triplex forming oligonucleotides, selective or targeted mutagens, and combinations thereof. The genetically engineered materials can be in solution, in suspension, incorporated into a plasmid or viral vector, and/or in a cell.

Gene transfer can be obtained using direct transfer of genetic material, in a plasmid or viral vector, or via transfer of genetic material in cells or carriers such as cationic liposomes. Such methods are well known in the art and readily adaptable for use in the gene mediated toxin therapies described herein. Further, these methods can be used to target certain diseases and cell populations by using the targeting characteristics of the carrier. Transfer vectors can be any nucleotide construction used to deliver genes into cells (e.g., a plasmid), or as part of a general strategy to deliver genes, e.g., as part of recombinant retrovirus or adenovirus (Ram et al. *Cancel Res.* 53: 83–88, 1993). Many types of cells can be transfected using these techniques and reagents. A preferred cell type for treatment of brain tumors is fibroblasts Bone marrow stem cells and hematopoietic cells are relatively easily removed and replaced from humans, and provide a self-regenerating population of cells for the propagation of transferred genes. When in vitro transfection of cells is performed, once the transfected cells begin producing the proteins encoded by the genes, the cells can be added back to the patient to establish entire pooled populations of cells that are expressing the transfected genes.

One of the most promising methods of gene transfer utilizes recombinant viruses. The development of recombinant adenoviruses as well as retroviral vectors for this purpose has had a number of applications. As used herein, a retrovirus is an animal virus belonging to the virus family of Retroviridae, including any types, subfamilies, genus, or tropisms. Retroviral vectors, in general, are described by Verma, I. M., Retroviral vectors for gene transfer. In MICROBIOLOGY-1985, American Society for Microbiology, pp. 229–232, Washington, 1985, which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, *Science* 260: 926–932 (1993); the teachings of which are incorporated herein by reference.

The construction of replication-defective adenoviruses is described by Berkner et al., 1987 *J. Virology* 61: 1213–1220 (1987); Massie et al., 1986 *Mol. Cell. Biol.* 6: 2872–2883 (1986); Haj-Ahmad et al., 1986 *J. Virology* 57: 267–274 (1986); Davidson et al., 1987 *J. Virology* 61: 1226–1239 (1987); Zhang "Generation and identification of recombinant adenovirus by liposome-mediated transfection and PCR analysis" *BioTechniques* 1993 15: 868–872. The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites, as reported by Morsy, 1993 *J. Clin. Invest.* 92: 1580–1586; Kirshenbaum, 1993 *J. Clin. Invest.* 92: 381–387; Roessler, 1993 *J. Clin. Invest.* 92: 1085–1092; Moullier, 1993 *Nature Genetics* 4: 154–159; La Salle, 1993 *Science* 259: 988–990; Gomez-Foix, 1992 *J. Biol. Chem.* 267: 25129–25134; Rich, 1993 *Human Gene Therapy* 4: 461–476; Zabner, 1994 *Nature Genetics* 6: 75–83; Guzman, 1993 *Circulation Research* 73: 1201–1207; Bout, 1994 *Human Gene Therapy* 5: 3–10; Zabner, 1993 *Cell* 75: 207–216; Caillaud, 1993 *Eur. J. Neuroscience* 5: 1287–1291; and Ragot, 1993 *J. Gen. Virology* 74: 501–507. Recombinant adenoviruses achieve gene transduction by binding to specific cell surface receptors, after which the virus is internalized by receptor-mediated endocytosis, in the same manner as wild type or replication-defective adenovirus, as reported by Chardonnet and Dales, 1970 *Virology* 40: 462–477; Brown and Burlingham, 1973 *J. Virology* 12: 386–396; Svensson and Persson, 1985 *J. Virology* 55: 442–449; Seth, et al., 1984 *J. Virol.* 51: 650–655; Seth, et al., *Mol. Cell. Biol.* 1984 4: 1528–1533; Varga et al., 1991 *J. Virology* 65: 6061–6070 (1991); Wickham et al., 1993 *Cell* 73: 309–319).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2: 447–451, 1991; Bagshawe, K. D., *Br. J. Cancer,* 60: 275–281, 1989; Bagshawe, et al., *Br. J. Cancer,* 58: 700–703, 1988; Senter, et al., *Bioconjugate Chem.*, 4: 3–9, 1993; Battelli, et al., *Cancer Immunol. Immunother.*, 35: 421–425, 1992; Pietersz and McKenzie, *Immunolog. Reviews,* 129: 57–80, 1992; and Roffler, et al., *Biochem. Pharmacol,* 42: 2062–2065, 1991. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49: 6214–6220, 1989; and Litzinger and Huang, *Biochimica et Biophysica Acta,* 1104: 179–187, 1992). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis is reviewed by Brown and Greene, *DNA and Cell Biology* 1991 10: 6, 399–409.

As discussed above, a strategy that has been developed to selectively kill tumor cells involves the delivery to replicating tumor cells and expression of genes encoding toxic prodrugs such as the HSV-tk gene followed by treatment with ganciclovir. Ganciclovir is readily phosphorylated by the HSV-tk, and its phosphorylated metabolites are toxic to the cell. Very little phosphorylation of ganciclovir occurs in normal human cells. Examples of other genetically engineered cells that can be delivered as described herein include cells transfected with the *E. coli* Deo D gene (purine nucleoside phosphorylase (PNP)) and subsequently treating with a nontoxic nucleoside analog (e.g., deoxyadenosine or deoxyguanosine analogs, including N7 analogs), which is converted to a toxic purine analog. *E. coli* PNP differs from human PNP in its acceptance of adenine- and certain guanine-containing nucleoside analogs as substrates. *E. coli* PNP expressed in tumor cells cleaves the nucleoside, liberating a toxic purine base analog. Purine bases freely diffuse across cell membranes, whereas nucleoside monophosphates generally remain inside the cell in which they are formed. The substrate administered to the cells is 9-(β-D-2-deoxyerythropentofuranosyl)-6-methylpurine (MeP-dR). A toxic adenine analog formed after conversion by *E. coli* PNP can be converted by adenine phosphoribosyl transferase to toxic nucleotides and kill all transfected cells, and diffuse out of the cell and kill surrounding cells that were not transfected (bystander cells).

Sites for Delivery

Although described herein primarily with reference to treatment of tumors, it will be understood by those skilled in the art that other tissues in need of treatment could be treated using the delivery system described herein. Tumors to be treated will generally be solid tumors, which can be located anywhere in the body. Tumors for which the delivery vehicle is particularly useful are brain tumors. Other tissues which can be treated include liver, pancreas, colon, lung, and nervous tissue, including normal and abnormal tissues in the central nervous system. As used herein, the term "tissue" will encompass both normal and transformed tissues, including solid tumors.

Density or Viscosity Modifying Materials

A variety of materials are known which can be adapted for use in the method described herein. It is not required that the material be biocompatible if the treatment is designed to kill tumors; for example, a vehicle which includes a cytotoxic compound such as ethanol may be used to facilitate delivery and efficacy of a chemotherapeutic agent to tumors.

Preferred materials are polymers which solidify or gel at the site of delivery. Polymeric solutions or suspensions can be formulated which solidify by formation of ionic or covalent coupling of the polymer, for example, through interactions with cations such as calcium, changes in pH, changes in temperature, and polymerization.

Polymer Solutions

The polymeric material which is mixed with cells or other materials for injection into the body should preferably form a hydrogel. A hydrogel is defined as a substance formed when an organic polymer (natural or synthetic) is crosslinked via covalent, ionic, or hydrogen bonds to create a three-dimensional open-lattice structure which entraps water molecules to form a gel. Naturally occurring and synthetic hydrogel forming polymers, polymer mixtures and copolymers may be utilized as hydrogel precursors. Examples of materials which can be used to form a hydrogel include polysaccharides such as alginate and modified alginates, synthetic polymers such as polyphosphazines, and polyacrylates, which are crosslinked ionically, or block copolymers such as Pluronics™ or Tetronics™, polyethylene oxide-polypropylene glycol block copolymers which are crosslinked by temperature or pH, respectively. Other materials include proteins such as fibrin, polymers such as polyvinylpyrrolidone, hyaluronic acid and collagen.

Natural Polymer Solutions

In one embodiment, the polymers are natural polymers such as proteins and polysaccharides. In the preferred embodiment, the protein solution is cryoprecipitate or fibrinogen derived from the patient to be treated. Proteins and polysaccharides can be ionically linked, typically by the addition of cations, crosslinked chemically for example using glutaraldehyde, or by chemical denaturation.

In a particularly preferred embodiment, cryoprecipitate is prepared from a plasma sample obtained directly from the patient. One unit of human blood consists of approximately 350 to 450 mls, which is preferably collected in ACD (citric acid-dextrose) anticoagulant, although other acceptable anticoagulants can be used such as ethylene diamine tetraacetate. The red blood cells are removed by centrifugation or filtration, and the separated plasma chilled at 4 C. until cryoprecipitate is formed, typically about three days. Cryoprecipitate consists predominantly of fibrinogen. Fresh frozen plasma can also be used.

Purified fibrinogen is also available from commercial suppliers such as Sigma Chemical Co., Baxter Diagnostics, and Ortho Pharmaceuticals. As used herein, the term "fibrinogen" is intended to encompass either cryoprecipitate or purified fibrinogen, unless specifically stated otherwise. Other materials that can be used as a source of fibrinogen besides cryoprecipitate, fresh frozen plasma, and purified fibrinogen, include factor VIII concentrate, platelet concentrate, and platelet rich plasma. Proteins other than fibrinogen can be substituted for the fibrinogen where the protein can be prepared and crosslinked using a physiologically acceptable crosslinker such as calcium. An advantage of the fibrinogen is that it is readily obtained in sufficient quantities merely by drawing blood from the intended recipient so that there is no problem with patient rejection of the implant or introduction of infectious agents harbored by the fibrinogen donor.

Alginate is a carbohydrate polymer isolated from seaweed, which can be crosslinked to form a hydrogel by exposure to a divalent cation such as calcium, as described, for example in WO 94/25080, the disclosure of which is incorporated herein by reference. Alginate is ionically crosslinked in the presence of divalent cations, in water, at room temperature, to form a hydrogel matrix. Due to these mild conditions, alginate has been the most commonly used polymer for hybridoma cell encapsulation, as described, for example, in U.S. Pat. No. 4,352,883 to Lim. In the Lim process, an aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

Examples of other materials which can be used to form a hydrogel include modified alginates. Modified alginate derivatives may be synthesized which have an improved ability to form hydrogels. The use of alginate as the starting material is advantageous because it is available from more than one source, and is available in good purity and characterization. As used herein, the term "modified alginates" refers to chemically modified alginates with modified hydrogel properties. Naturally occurring alginate may be chemical modified to produce alginate polymer derivatives that degrade more quickly. For example, alginate may be chemically cleaved to produce smaller blocks of gellable oligosaccharide blocks and a linear copolymer may be formed with another preselected moiety, e.g. lactic acid or ε-caprolactone. The resulting polymer includes alginate blocks which permit ionically catalyzed gelling, and oligoester blocks which produce more rapid degradation depending on the synthetic design. In the embodiment wherein modified alginates and other anionic polymers that can form hydrogels which are malleable are used to encapsulate cells, the hydrogel is produced by cross-linking the polymer with the appropriate cation, and the strength of the hydrogel bonding increases with either increasing concentrations of cations or of polymer. Concentrations from as low as 0.001 M have been shown to cross-link alginate. Higher concentrations are limited by the toxicity of the salt. Alternatively, alginate polymers may be used, wherein the ratio of mannuronic acid to guluronic acid does not produce a firm gel, which are derivatized with hydrophobic, water-labile chains, e.g., oligomers of ε-caprolactone. The hydrophobic interactions induce gelation, until they degrade in the body.

Additionally, polysaccharides which gel by exposure to monovalent cations, including bacterial polysaccharides, such as gellan gum, and plant polysaccharides, such as carrageenans, may be crosslinked to form a hydrogel using methods analogous to those available for the crosslinking of alginates described above. Polysaccharides which gel in the presence of monovalent cations form hydrogels upon exposure, for example, to a solution comprising physiological levels of sodium. Hydrogel precursor solutions also may be osmotically adjusted with a nonion, such as mannitol, and then injected to form a gel.

Synthetic Ionically Cross-Linkable Polymers

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups. Methods for the synthesis of the polymers described above are known to those skilled in the art. See, for example Concise Encyclopedia of Polymer Science and Polymeric Amines and Ammonium Salts, E. Goethals, editor (Pergamen Press, Elmsford, N.Y. 1980). Many polymers, such as poly(acrylic acid), are commercially available.

The water soluble polymer with charged side groups is crosslinked by reacting the polymer with an aqueous solution containing multivalent ions of the opposite charge, either multivalent cations if the polymer has acidic side groups or multivalent anions if the polymer has basic side groups. Examples of cations for cross-linking of the polymers with acidic side groups to form a hydrogel are monovalent cations such as sodium, and multivalent cations such as copper, calcium, aluminum, magnesium, strontium, barium, and tin, and di-, tri- or tetra-functional organic cations such as alkylammonium salts. The preferred cations for cross-linking of the polymers with acidic side groups to form a hydrogel are divalent and trivalent cations such as copper, calcium, aluminum, magnesium, strontium, barium, and tin. Aqueous solutions of the salts of these cations are added to the polymers to form soft, highly swollen hydrogels and membranes. Aqueous solutions of the salts of these cations are added to the polymers to form soft, highly swollen hydrogels and membranes. The higher the concentration of cation, or the higher the valence, the greater the degree of cross-linking of the polymer. Concentrations from as low as 0.005 M have been demonstrated to cross-link the polymer. Higher concentrations are limited by the solubility of the salt.

The preferred anions for cross-linking of the polymers to form a hydrogel are monovalent, divalent or trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine); examples of synthetic polyamines are: polyethyleneimine, poly(vinylamine), and poly(allyl amine). There are also natural polycations such as the polysaccharide, chitosan.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups.

Synthetic Polymers Crosslinkable by Hydrogen Bonding

Other polymeric hydrogel precursors include polyethylene oxide-polypropylene glycol block copolymers such as Pluronics™ or Tetronics™, which are crosslinked by hydrogen bonding and/or by a temperature change, as described in Steinleitner et al., Obstetrics & Gynecology, 77: 48–52 (1991); and Steinleitner et al., Fertility and Sterility, 57: 305–308 (1992).

Polymer mixtures also may be utilized. For example, a mixture of polyethylene oxide and polyacrylic acid which gels by hydrogen bonding upon mixing may be utilized. In one embodiment, a mixture of a 5% w/w solution of polyacrylic acid with a 5% w/w polyethylene oxide (polyethylene glycol, polyoxyethylene) 100,000 can be combined to form a gel over the course of time, e.g., as quickly as within a few seconds.

Synthetic Covalently Crosslinkable Polymers

Covalently crosslinkable hydrogel precursors also are useful. For example, a water soluble polyamine, such as chitosan, can be cross-linked with a water soluble diisothiocyanate, such as polyethylene glycol diisothiocyanate. The isothiocyanates will react with the amines to form a chemically crosslinked gel. Aldehyde reactions with amines, e.g., with polyethylene glycol dialdehyde also may be utilized. A hydroxylated water soluble polymer also may be utilized.

Alternatively, polymers may be utilized which include substituents which are crosslinked by a radical reaction upon contact with a radical initiator. For example, polymers including ethylenically unsaturated groups which can be photochemically crosslinked may be utilized, as disclosed in WO 93/17669, the disclosure of which is incorporated herein by reference. In this embodiment, water soluble macromers that include at least one water soluble region, a biodegradable region, and at least two free radical-polymerizable regions, are provided. The macromers are polymerized by exposure of the polymerizable regions to free radicals generated, for example, by photosensitive chemicals and or light. Examples of these macromers are PEG-oligolactyl-acrylates, wherein the acrylate groups are polymerized using radical initiating systems, such as an eosin dye, or by brief exposure to ultraviolet or visible light. Additionally, water soluble polymers which include cinnamoyl groups which may be photochemically crosslinked may be utilized, as disclosed in Matsuda et al., *ASAID Trans.*, 38–157 (1992).

Density Modifying Agents

Although described herein particularly with reference to polymers which increase the viscosity and/or density of the material to be injected into the tissue to be treated, other materials could also be used which are not polymers. Many agents which increase viscosity or density are routinely used, especially in the food and medical industry. Generally, these include proteins such as albumin, sugars such as dextran, glucose and fructose, and strarches, although these are technically polymers. As used herein, the term "polymers" encompasses the addition of monomers or single unit material that function to increase the viscosity and/or density of the solution to be injected into the tissue to be treated.

Polysaccharides that are very viscous liquids or are thixotropic, and form a gel over time by the slow evolution of structure, are especially useful. For example, hyaluronic acid, which forms an injectable gel with a consistency like a hair gel, may be utilized. Modified hyaluronic acid derivatives are particularly useful. As used herein, the term "modified hyaluronic acids" refers to chemically modified hyaluronic acids. Modified hyaluronic acids may be designed and synthesized with preselected chemical modifications to adjust the rate and degree of crosslinking and biodegradation. For example, modified hyaluronic acids may be designed and synthesized which are esterified with a relatively hydrophobic group such as propionic acid or benzylic acid to render the polymer more hydrophobic and gel-forming, or which are grafted with amines to promote electrostatic self-assembly. Modified hyaluronic acids thus may be synthesized which are injectable, in that they flow under stress, but maintain a gel-like structure when not under stress. Hyaluronic acid and hyaluronic derivatives are available from Genzyme, Cambridge, Mass. and Fidia, Italy.

Other materials that are dense and/or viscous include many of the lipids and sterols such as cholesterol, oils and fats.

Cell Suspensions

Preferably the polymer or density modifying agent is dissolved in an aqueous solution, preferably a 0.1 M potassium phosphate solution, at physiological pH, to a concentration yielding the desired density, for example, for alginate, of between 0.5 to 2% by weight, preferably 1%, alginate. The isolated cells are suspended in the polymer solution to a concentration of between 1 and 100 million cells/ml, most preferably approximately 100 million cells/ml. In a preferred embodiment, the polymer is fibrinogen and the cells are added to one ml of commercially available thrombin to a concentration of 100 million cells, then added to an equivalent volume of fibrinogen for injection into the tumor.

Combinations of materials increasing viscosity and density, as described above, may also be utilized.

Additives

A variety of materials can be added to the polymer-cell solution. Examples of useful materials include proteins, polysaccharides, nucleic acids, vitamins and metals or ions (calcium, sodium and potassium), and synthetic organic molecules. Examples include enzymes such as collagenase inhibitors, hemostatic agents such as thrombin, fibrinogen or calcium ions, growth factors, angiogenic factors and other growth effector molecules, bacteriostatic or bacteriocidal factors, antiinflammatories, anti-angiogenic agents, and vitamins. Growth effector molecules, as used herein, refer to molecules that bind to cell surface receptors and regulate the growth, replication or differentiation of target cells or tissue. Preferred growth effector molecules are growth factors and extracellular matrix molecules. Examples of growth factors include epidermal growth factor (EGF), platelet-derived growth factor (PDGF), transforming growth factors (TGFá, TGFâ), hepatocyte growth factor, heparin binding factor, insulin-like growth factor I or II, fibroblast growth factor (FGF), VEGF, LPA, erythropoietin, nerve growth factor, bone morphogenic proteins, muscle morphogenic proteins, and other factors known to those of skill in the art. Additional growth factors are described in "Peptide Growth Factors and Their Receptors I" M. B. Sporn and A. B. Roberts, eds. (Springer-Verlag, New York, 1990), for example, the teachings of which are incorporated by reference herein. Growth factors which are preferred when the material to be injected is fibroblasts, especially skin fibroblasts, are EGF and FGF. Many growth factors are also available commercially from vendors, such as Sigma Chemical Co. of St. Louis, Mo., Collaborative Research, Genzyme, Boehringer, R&D Systems, and GIBCO, in both natural and recombinant forms. Examples of extracellular matrix molecules include fibronectin, laminin, collagens, and proteoglycans. Other extracellular matrix molecules are described in Kleinman et al. (1987) or are known to those skilled in the art. Other growth effector molecules include cytokines, such as the interleukins and GM-colony stimulating factor, and hormones, such as insulin. These are also described in the literature and are commercially available. Collagenase inhibitors, including tissue inhibitor metalloproteinase (TIMP), may also be useful as growth effector molecules. Examples of hemostatic agents include thrombin, Factor Xa, fibrinogen, and calcium ions, typically in the form of calcium chloride or calcium gluconate. Vasoconstrictive agents such as epinephrine can also be used to contract blood vessels and thereby decrease bleeding. Bacteriostatic and bacteriocidal agents include antibiotics and other compounds used for preventing or treating infection in wounds.

The bioactive agents are typically incorporated in a range of nanograms to micrograms in a volume of 0.1 ml, although they can also be applied in dry form, as a paste or suspension.

Modifications and variations of the present invention will be obvious to those skilled in the art from the foregoing detailed description. Such modifications and variations are intended to come within the scope of the appended claims.

I claim:

1. A method for enhancing the delivery of cytotoxic genetically engineered cells, the improvement comprising adding to the cytotoxic genetically engineered cells an injectable polymeric composition which gels or solidifies at the time of or shortly after injection and has a consistency and density effective to displace the cells at a site where the genetically engineered cells are injected and effective to retain the genetically engineered cells at the site of injection.

2. The method of claim 1 wherein the cells are genetically engineered to express a bioactive protein.

3. The method of claim 2 wherein the genetically engineered cells comprise a plasmid or viral expression vector.

4. The method of claim 1 wherein the polymeric composition is a polymer solution which is ionically crosslinkable under physiological conditions by addition of ions.

5. The method of claim 1 wherein the polymeric composition is a polymer solution which is covalently crosslinkable under physiological conditions by addition of a crosslinking agent.

6. The method of claim 1 wherein the viscosity of the polymeric composition is increased under physiological conditions of pH or temperature.

7. The method of claim 1 wherein the polymeric composition is selected from the group consisting of proteins, polysaccharides, and synthetic polymers.

8. The method of claim 7 wherein the polymeric composition is fibrinogen or cryoprecipitate.

9. The method of claim 7 wherein the polymer is selected from the group consisting of poly(phosphazenes), poly(acrylic acids), poly(methacrylic acids), copolymers of acrylic acid and methacrylic acid, poly(vinyl acetate), and sulfonated polymers, and alginates.

10. A composition for enhancing the delivery of cytotoxic genetically engineered cells, the improvement comprising an injectable polymeric vehicle which gels or solidifies at the time of or shortly after injection and has a consistency and density effective to displace the cells at a site where the genetically engineered cells are to be delivered and to retain the genetically engineered cells at the site of injection.

11. The composition of claim 10 wherein the cells are genetically engineered to express a bioactive protein.

12. The composition of claim 11 wherein the genetically engineered cells comprise a plasmid or viral expression vector.

13. The composition of claim 10 wherein the polymeric composition is a polymer solution which is ionically crosslinkable under physiological conditions by addition of ions.

14. The composition of claim 10 wherein the polymeric composition is a polymer solution which is covalently crosslinkable under physiological conditions by addition of a crosslinking agent.

15. The composition of claim 10 wherein the viscosity of the polymeric composition is increased under physiological conditions of pH or temperature.

16. The composition of claim 10 wherein the polymeric composition is selected from the group consisting of proteins, polysaccharides, and synthetic polymers.

17. The composition of claim 16 wherein the polymeric composition is fibrinogen or cryoprecipitate.

18. The composition of claim 16 wherein the polymer is selected from the group consisting of poly(phosphazenes), poly(acrylic acids), poly(methacrylic acids), copolymers of acrylic acid and methacrylic acid, poly(vinyl acetate), and sulfonated polymers, and alginates.

* * * * *